US010502332B2

(12) United States Patent
Black et al.

(10) Patent No.: US 10,502,332 B2
(45) Date of Patent: Dec. 10, 2019

(54) DUCKBILL VALVE ASSEMBLIES AND APPARATUS AND METHODS INCLUDING SAME

(71) Applicant: PerkinElmer Health Sciences, Inc., Waltham, MA (US)

(72) Inventors: Benjamin J. Black, West Valley City, UT (US); Anthony David Rands, Vineyard, UT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 15/949,337

(22) Filed: Apr. 10, 2018

(65) Prior Publication Data

US 2019/0309863 A1   Oct. 10, 2019

(51) Int. Cl.
*F16K 15/14* (2006.01)
*B01L 3/00* (2006.01)

(52) U.S. Cl.
CPC ............ *F16K 15/147* (2013.01); *B01L 3/565* (2013.01); *B01L 3/567* (2013.01); *B01L 2200/0689* (2013.01); *B01L 2400/0611* (2013.01)

(58) Field of Classification Search
CPC .. B01L 3/565; B01L 3/567; B01L 2200/0689; B01L 2400/0611; F16K 15/147
(Continued)

(56) References Cited

U.S. PATENT DOCUMENTS 2,526,629 A * 10/1950 Bourke ................ B67D 1/0832
137/847
4,524,805 A   6/1985 Hoffman
(Continued)

FOREIGN PATENT DOCUMENTS

CN   105416812   3/2016
WO   96/09539   3/1996

OTHER PUBLICATIONS

Notification of Transmittal of the International Search Report and the Written Opinion of the International Searching Authority, or the Declaration, in corresponding PCT Application No. PCT/US2019/019367 (dated Jun. 4, 2019).

*Primary Examiner* — P. Macade Nichols
(74) *Attorney, Agent, or Firm* — Myers Bigel, P.A.

(57) ABSTRACT

A duckbill valve assembly includes a duckbill valve and a spring member. The duckbill valve has a longitudinal axis, a lateral axis transverse to the longitudinal axis, and opposed proximal and distal ends spaced apart along the longitudinal axis. The duckbill valve defines a valve direction extending from the proximal end to the distal end. The duckbill valve includes a first port at the proximal end, and first and second opposed sidewalls. The first and second sidewalls taper inwardly toward one another in the valve direction to form a duckbill structure. The duckbill structure includes a slit proximate the distal end. The duckbill valve is transitionable from a closed position, wherein the slit is closed, and an open position, wherein the first and second sidewalls are laterally separated proximate the slit to form a second port. The spring member includes a spring leg disposed laterally adjacent the first side wall. The spring leg exerts a spring load on the first sidewall, the spring load forcing the first and second sidewalls together to maintain the slit in the closed position. The duckbill valve assembly is configured such that, when the first and second sidewalls are displaced laterally outward to open the slit, the spring leg is displaced in the valve direction and in a laterally outward direction.

19 Claims, 12 Drawing Sheets

(58) Field of Classification Search
USPC .......................................................... 137/847
See application file for complete search history.

(56) References Cited

U.S. PATENT DOCUMENTS

| | | |
|---|---|---|
| 4,954,149 A | 9/1990 | Fullemann |
| 5,531,810 A | 7/1996 | Fullemann |
| 6,092,551 A | 7/2000 | Bennett |
| 8,276,616 B2 | 10/2012 | Wright et al. |
| 9,322,750 B2 | 4/2016 | Oliphant et al. |
| 2007/0244426 A1 | 10/2007 | Hart et al. |

* cited by examiner

DUCKBILL VALVE ASSEMBLIES AND APPARATUS AND METHODS INCLUDING SAME

FIELD

The present technology relates to gas seals and, more particularly, to duckbill valves.

BACKGROUND

Gas chromatography is commonly used in analytical chemistry for separating and analyzing compounds of a sample. For example, a gas chromatograph may be used to test the purity of a sample, identify a compound, separate different components of a mixture or to prepare (e.g., purify) compounds from a mixture. Gas chromatography is essentially a physical method of separation in which constituents of a test sample in a carrier gas are absorbed and desorbed by a stationary phase material in a column. A plug of the sample is injected into a steady flow of carrier gas. Interactions between this stationary phase material and the various components of the sample—which differ based upon differences among partition coefficients of the components—cause the sample to be separated into the respective components. At the end of the column the individual components are more or less separated in time. Detection of the vapors provides a time-scaled pattern which, by calibration or comparison with known samples, indicates the constituents and their concentrations in the test sample.

Typically, the main components of such a system are the column, an injector for introducing the sample into carrier gas and passing the mixture into the column, a device for transferring sample into the injector, a detector at the outer end of the column, gas controls, and a device such as a computer for processing and displaying the output of the detector. An oven may be used to elevate temperature to maintain the sample in a volatile state, and to improve the discrimination of constituents. The injector may include a resealable septum through which a needle can be inserted to inject a sample into the injector.

It is also known to provide gastight, resealable septa on vials used to contain samples.

SUMMARY

According to some embodiments of the technology, a duckbill valve assembly includes a duckbill valve and a spring member. The duckbill valve has a longitudinal axis, a lateral axis transverse to the longitudinal axis, and opposed proximal and distal ends spaced apart along the longitudinal axis. The duckbill valve defines a valve direction extending from the proximal end to the distal end. The duckbill valve includes a first port at the proximal end, and first and second opposed sidewalls. The first and second sidewalls taper inwardly toward one another in the valve direction to form a duckbill structure. The duckbill structure includes a slit proximate the distal end. The duckbill valve is transitionable from a closed position, wherein the slit is closed, and an open position, wherein the first and second sidewalls are laterally separated proximate the slit to form a second port. The spring member includes a spring leg disposed laterally adjacent the first side wall. The spring leg exerts a spring load on the first sidewall, the spring load forcing the first and second sidewalls together to maintain the slit in the closed position. The duckbill valve assembly is configured such that, when the first and second sidewalls are displaced laterally outward to open the slit, the spring leg is displaced in the valve direction and in a laterally outward direction.

According to some embodiments, the spring member includes a base portion and a spring leg cantilevered from the base portion. The spring leg has a proximal end joined to the base portion and a distal end that applies the spring load to the first sidewall.

In some embodiments, the duckbill valve assembly includes a radiused bend forming a hinge connecting the proximal end of the spring leg to the base portion.

According to some embodiments, the radiused bend has a radius in the range of from about 0.7 mm to 0.9 mm.

According to some embodiments, the spring leg includes a rounded bearing surface proximate the distal end of the spring leg, and the rounded bearing surface engages the first sidewall.

In some embodiments, the rounded bearing surface has a radius in the range of from about 0.4 mm to 0.6 mm.

According to some embodiments, the spring leg has opposed axially ending side edges that taper inwardly in a direction from the base portion to the distal end.

In some embodiments, the duckbill valve assembly includes a support and a clamp member, wherein the base portion is clamped between the support and the clamp member.

According to some embodiments, the spring member includes a second spring leg disposed laterally adjacent the second side wall and laterally opposite the first spring leg. The second spring leg exerts a second spring load on the second sidewall, the first and second spring loads forcing the first and second sidewalls together to maintain the slit in the closed position. The duckbill valve assembly is configured such that, when the first and second sidewalls are displaced laterally outward to open the slit, the first and second spring legs are displaced in the valve direction and in opposing laterally outward directions.

In some embodiments, the spring member includes a base portion having opposed first and second side edges. The first spring leg is cantilevered from the first side edge of the base portion. The first spring leg has a proximal end joined to the base portion and a distal end that applies the first spring load to the first sidewall. The second spring leg is cantilevered from the second side edge of the base portion. The second spring leg has proximal end joined to the base portion and a distal end that applies the second spring load to the second sidewall.

According to some embodiments, the duckbill valve assembly includes first and second radiused bends. The first radiused bend forms a hinge connecting the proximal end of the first spring leg to the first side edge of the base portion. The second radiused bend forms a hinge connecting the proximal end of the second spring leg to the second side edge of the base portion.

In some embodiments, the spring member is monolithic.

According to some embodiments, the duckbill valve assembly includes a supplemental ring seal.

According to embodiments of the technology, an apparatus includes a chamber and a duckbill valve assembly. The duckbill valve assembly is positioned to control fluid flow into and/or out of the chamber. The duckbill valve assembly includes a duckbill valve and a spring member. The duckbill valve has a longitudinal axis, a lateral axis transverse to the longitudinal axis, and opposed proximal and distal ends spaced apart along the longitudinal axis. The duckbill valve defines a valve direction extending from the proximal end to the distal end. The duckbill valve includes a first port at the proximal end, and first and second opposed sidewalls. The first and second sidewalls taper inwardly toward one another in the valve direction to form a duckbill structure. The duckbill structure includes a slit proximate the distal end. The duckbill valve is transitionable from a closed position, wherein the slit is closed, and an open position, wherein the first and second sidewalls are laterally separated proximate the slit to form a second port. The spring member includes a spring leg disposed laterally adjacent the first side wall. The spring leg exerts a spring load on the first sidewall, the spring load forcing the first and second sidewalls together to maintain the slit in the closed position. The duckbill valve assembly is configured such that, when the first and second sidewalls are displaced laterally outward to open the slit, the spring leg is displaced in the valve direction and in a laterally outward direction.

According to some embodiments, the apparatus is a needle trap charging module.

In some embodiments, the apparatus is a gas chromatograph injector.

In some embodiments, the apparatus is a vial.

According to method embodiments of the technology, a method for handling a fluid includes providing an apparatus including a chamber and a duckbill valve assembly. The duckbill valve assembly is positioned to control fluid flow into and/or out of the chamber. The duckbill valve assembly includes a duckbill valve and a spring member. The duckbill valve has a longitudinal axis, a lateral axis transverse to the longitudinal axis, and opposed proximal and distal ends spaced apart along the longitudinal axis. The duckbill valve defines a valve direction extending from the proximal end to the distal end. The duckbill valve includes a first port at the proximal end, and first and second opposed sidewalls. The first and second sidewalls taper inwardly toward one another in the valve direction to form a duckbill structure. The duckbill structure includes a slit proximate the distal end. The duckbill valve is transitionable from a closed position, wherein the slit is closed, and an open position, wherein the first and second sidewalls are laterally separated proximate the slit to form a second port. The spring member includes a spring leg disposed laterally adjacent the first side wall. The spring leg exerts a spring load on the first sidewall, the spring load forcing the first and second sidewalls together to maintain the slit in the closed position. The duckbill valve assembly is configured such that, when the first and second sidewalls are displaced laterally outward to open the slit, the spring leg is displaced in the valve direction and in a laterally outward direction. The method further includes: inserting an elongate member through the duckbill valve assembly and into the chamber; using the elongate member, extracting a fluid from the chamber and/or introducing a fluid into the chamber; and thereafter removing the elongate member from the duckbill valve assembly.

In some embodiments, the elongate member is a needle.

In some embodiments, the needle forms a part of a needle trap.

Further features, advantages and details of the present technology will be appreciated by those of ordinary skill in the art from a reading of the figures and the detailed description of the preferred embodiments that follow, such description being merely illustrative of the present technology.

DETAILED DESCRIPTION

Figure 1:
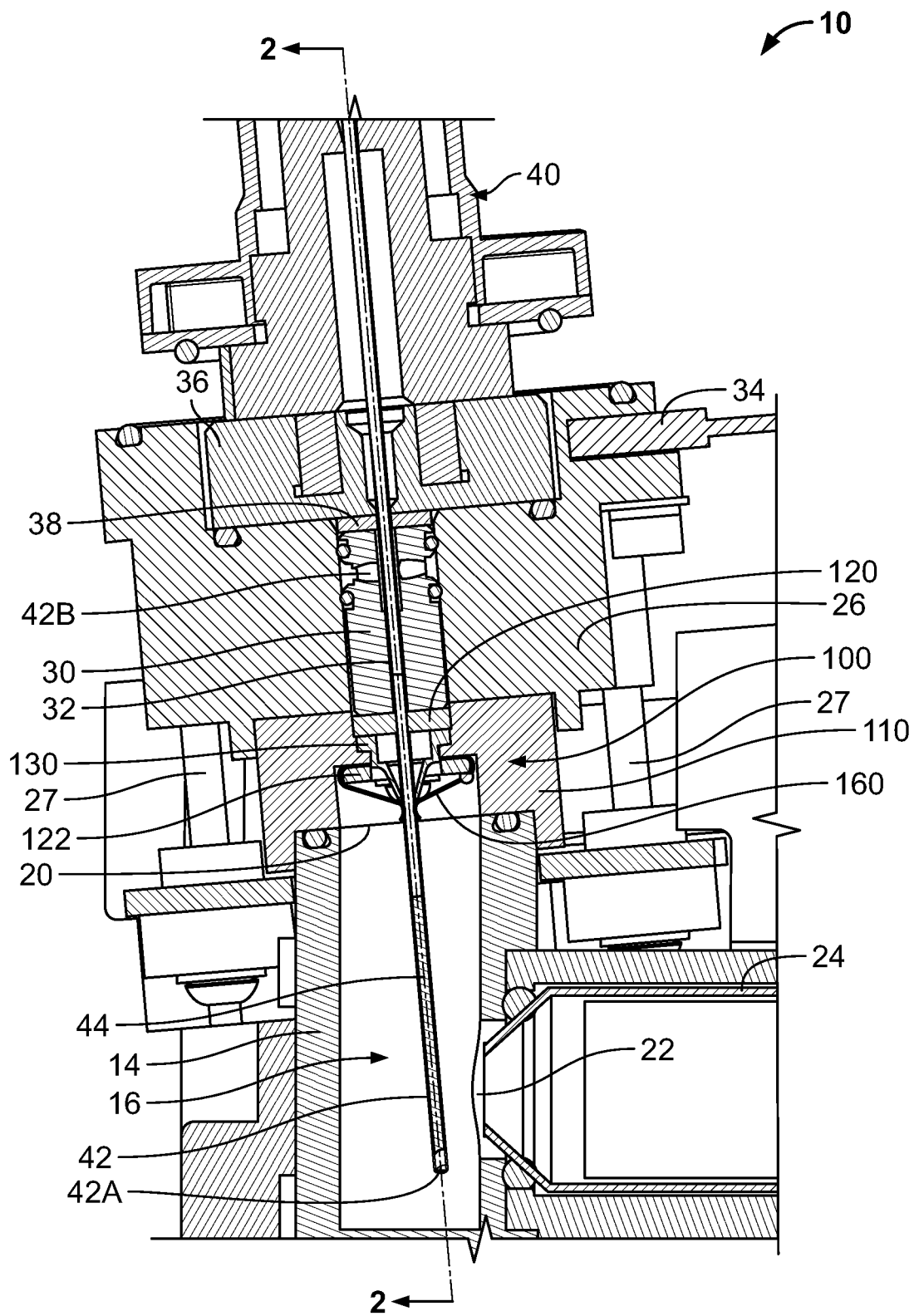
FIG. 1 is a cross-sectional view of a needle trap charging module including a duckbill valve assembly according to embodiments of the technology.
Figure 2:
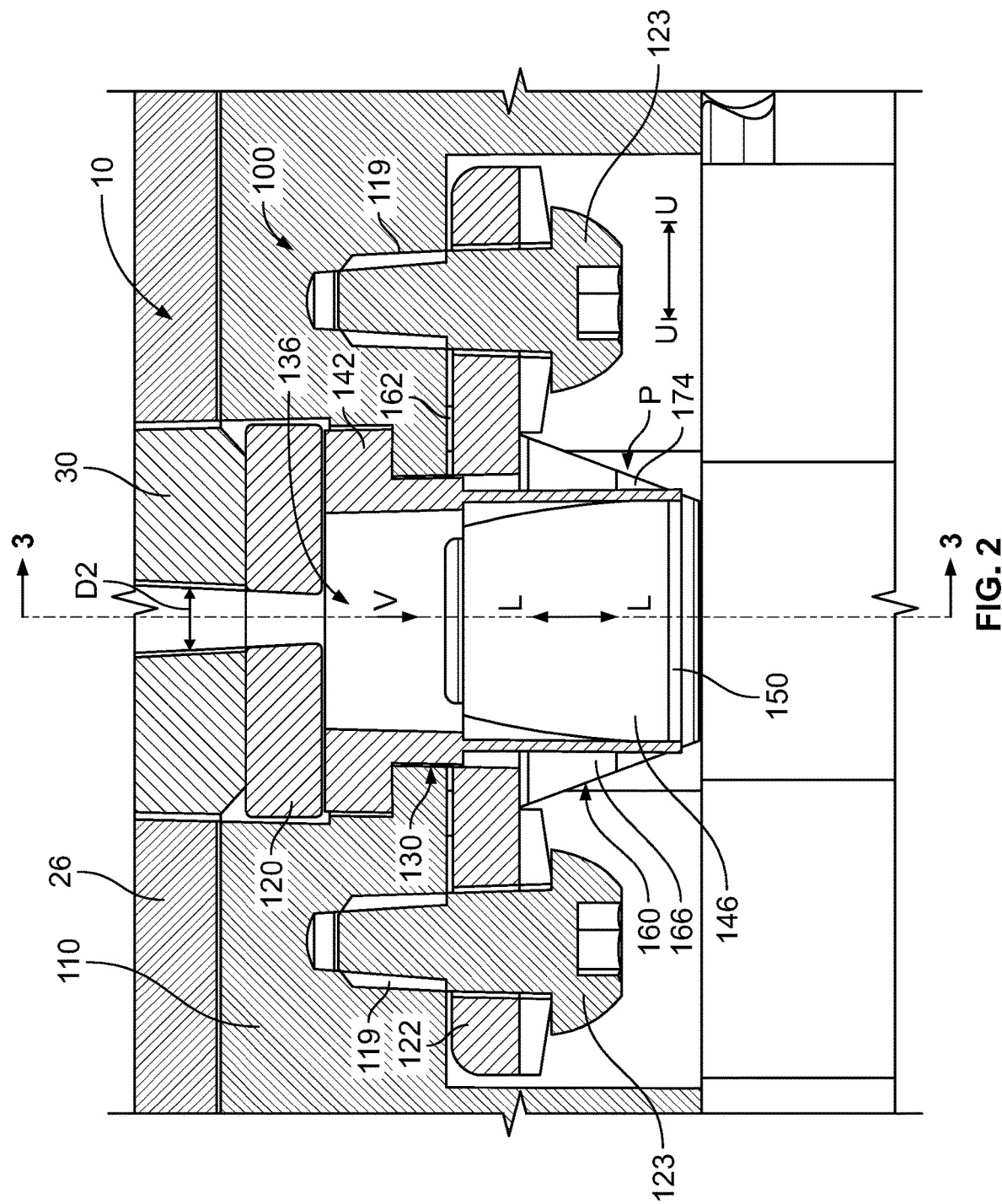
FIG. 2 is an enlarged, fragmentary, cross-sectional view of the needle trap charging module of FIG. 1 taken along the line 2-2 of FIG. 1 and showing the duckbill valve assembly.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

As used herein, "monolithic" means an object that is a single, unitary piece formed or composed of a material without joints or seams. Alternatively, a unitary object can be a composition composed of multiple parts or components secured together at joints or seams.

With reference to FIGS. 1-10, a needle trap charging or loading module 10 according to embodiments of the technology is shown therein. The module 10 includes a duckbill valve assembly 100 according to embodiments of the technology. The duckbill valve assembly 100 operates as a gas tight, resealable septum to limit or prevent unintended discharge of a gas or gases from the module 10.

The module 10 includes a body 14 including a headspace or chamber 16. A top opening 20 and a side port 22 fluidly communicate with the chamber 16. In use, a container 24 (e.g., a vial) is mounted such that the contents of the container 24 are in fluid communication with the chamber 16 through the side port 22.

The module 10 further includes a head 26 mounted on the body 14. The head 26 includes a gas exit port 34. A needle guide 30 is mounted in the head 26. The needle guide 30 includes a central needle passage 32. An endcap 36 is a fixed to the head 26 above the needle guide 30. An annular seal member 38 is captured between the needle guide 30 and the endcap 36.

The module 10 may be used with a needle trap 40. The needle trap 40 includes a needle 42 and a trap media 44. In some embodiments, the media 44 is disposed in the needle 42. However, it will be appreciated from the disclosure herein that needle traps of other designs and other instruments may be used with the module 10 and valve assembly 100 in accordance with embodiments of the technology.

The valve assembly 100 includes a support 110, an annular ring seal 120, a clamp plate 122, a duckbill valve or valve member 130, and a spring or spring member 160.

The support 110 includes a body 111. A through hole 112 is defined in the body 111. An outer bore 114 and an inner bore 116 are defined on opposed sides of the through hole 112 and form an annular flange 118 therebetween. A pair of bolt holes 119 are defined in the underside of the body 111 in the bore 116.

The support 110 may be formed of any suitable material. According to some embodiments, the support 110 is formed of a thermoplastic such as a polyetherimide resin (e.g., ULTEM™ PEI resin available from SABIC) in some embodiments, the support 110 is monolithic.

In some embodiments, the valve assembly 100 is secured by clamping the support 110 in place between the head 26 and the containment body 14 using clamp bolts 27. However, other means for securing the valve assembly 100 in place may be used. Suitable sealing devices (e.g., O-rings) may be provided between the respective components to ensure a gas tight enclosure.

The ring seal 120 may be annular, cylindrical or doughnut shaped and includes a through opening 120A. The ring seal 120 may be formed of any suitable material or materials. In some embodiments, the ring seal 120 is formed of an elastomeric material. In some embodiments, the valve member is formed of a fluoropolymer elastomer such as VITON™ elastomer available from FKM. In some embodiments, the ring seal 120 is unitarily formed. In some embodiments, the valve number is monolithic.

The valve member 130 (FIG. 7) has a longitudinal axis L-L (FIG. 3), a lateral axis T-T (FIG. 3) extending perpendicular to the axis L-L, and a fore-aft axis U-U (FIG. 2) extending perpendicular to each of the axes L-L and T-T. The valve member 130 has a proximal end 132A and an opposing distal end 132B axially spaced apart from the proximal end 132A. The valve member 130 has a valve direction extending along the longitudinal axis L-L in the direction from the proximal end 132A to the distal end 132B.

The valve member 130 includes an annular or cylindrical body 140. An integral, annular flange 142 projects radially outwardly from the body 140 at the proximal end 132A. An integral duckbill structure 144 extends axially downwardly from the body 140.

A first or outer port 136 is defined in the body 140 at the proximal end 132A. A second or inner port 138 is defined in the duckbill structure 144 at the distal end 132B.

The duckbill structure 144 includes opposed, flat flaps, lips or sidewalls 146 and 148 that extend obliquely to the longitudinal axis L-L. Each of the sidewalls 146, 148 has a proximal end connected or merged to the body 140 and terminates at a distal terminal edge 149 at the distal end 132B. The sidewalls 144, 146 taper inwardly toward one another in an axial direction from the proximal end 132A to the distal end 132B (i.e., in the valve direction V).

The sidewalls 146 and 148 have outwardly facing exterior surfaces 146A and 148A, respectively. The sidewalls 146 and 148 have inwardly facing interior closure surfaces 146B and 148B, respectively.

A slit 150 is defined in the terminal edge 149. The slit 150 extends generally along an axis parallel to the fore-aft axis U-U. The sidewalls 146, 148 are deformable or flexible to permit the sidewalls 146, 148 to separate from one another and open the slit 150. As discussed herein, the slit 150 can assume each of a closed position (FIGS. 1-3 and 7) and one or more open positions (FIG. 4). In an open position, the slit 150 forms the second port 138.

In some embodiments, the slit 150 has a length L3 (FIG. 7) in the range of from about 3.8 mm to 4.2 mm.

The valve member 130 may be formed of any suitable material or materials. In some embodiments, the valve member 130 is formed of an elastomeric material. In some embodiments, the valve member is formed of a fluoropolymer elastomer such as VITON™ elastomer. In some embodiments, the valve member 130 is unitarily formed. In some embodiments, the valve number is monolithic.

The spring member 160 includes a base portion 162, a first spring leg 166, and an opposing second spring leg 168. In some embodiments, the base portion 162 and the spring legs 166, 168 are each formed as flat plate structures or sections having relatively thin thicknesses.

The base portion 162 may be substantially flat or planar. The base portion 162 has opposed side edges 162A, 162B that extend substantially parallel to the fore-aft axis U-U. A through hole 163 is defined in the base portion 162.

Each spring leg 166, 168 has a proximal end 166A, 168A and a distal end 166B, 168B.

The proximal end 166A of the spring leg 166 is joined to the side edge 162A at a hinge 170 so that the spring leg 166 is cantilevered from the base portion 162. The proximal end 168A of the spring leg 168 is joined to the side edge 162B at a hinge 170 so that the spring leg 168 is likewise cantilevered from the base portion 162.

Each of the hinges 170 is formed by a bend 172. According to some embodiments and as shown, each bend 172 is radiused. In some embodiments, the profile of each bend 172 is a smooth curve from the edge 162A, 162B to the leg proximal end 166A, 168A.

In some embodiments, each bend 172 has a radius R2 (FIG. 9) of at least 0.8 mm. In some embodiments, each bend 172 has a radius R2 in the range of from about 0.7 mm to 0.9 mm.

Each spring leg 166, 168 has, at its distal end 166B, 168B, an engagement portion 174 and a flared section 176 extending from the engagement portion 174 to a terminal edge 178. The engagement portions 174 may be formed by bends, as shown.

Each engagement portion 174 includes an inner contact or engagement surface 173. Each engagement surface 173 as a rounded profile. In some embodiments, the profile of each engagement surface 173 is a smooth curve.

In some embodiments, each contact surface 173 has a radius R3 (FIG. 9) of at least 0.4 mm. In some embodiments, each contact surface has a radius R3 in the range of from about 0.4 mm to 0.6 mm.

In some embodiments, each spring leg 166, 168, forms an oblique angle A1 (FIG. 9) with the longitudinal axis L-L. In some embodiments, the angle A1 is in the range of from about 66 degrees to 70 degrees.

In some embodiments, each spring leg 166, 168, has a length L1 (FIG. 9) in the range of from about 5.9 mm to 6.3 mm The spring member 160 may be formed of any suitable material or materials. In some embodiments, the spring member 160 is formed of metal. In some embodiments, the spring member 160 is formed of a material selected from the group consisting of steel (e.g., 301 stainless spring steel). In some embodiments, the spring member 160 is unitarily formed. In some embodiments, the spring member 160 is monolithic. In some embodiments, the spring member 160 is formed of a thin metal sheet that is bent or formed into the configuration of FIGS. 8-10. In some embodiments, the spring member 160 has a thickness T1 (FIG. 9) in the range of from about 0.12 mm to 0.14 mm.

The clamp plate 122 is a substantially flat member. A central hole 122A and fastener holes 122B are defined in the clamp plate 122.

The clamp plate 122 may be formed of any suitable material or materials. In some embodiments, the clamp plate 122 is formed of metal. In some embodiments, the clamp plate 122 is formed of a material selected from the group consisting of steel (e.g., 300 series stainless steel).

The spring member 160 is affixed to the underside of the support 110 in the inner bore 116 by the clamp plate 122 and fasteners 123 (e.g., bolts). The fasteners 123 extend through the holes 122B and are anchored in the bolt holes 119. The spring base 162 is clamped tightly and flat between the clamp plate 122 and the support 110.

The valve member 130 is inserted through the through hole 112 such that the flange 142 is seated against the flange 118, the body 140 and duckbill 144 extend through the openings 112, 162A, and 122A and into the inner bore 116.

Figure 3:
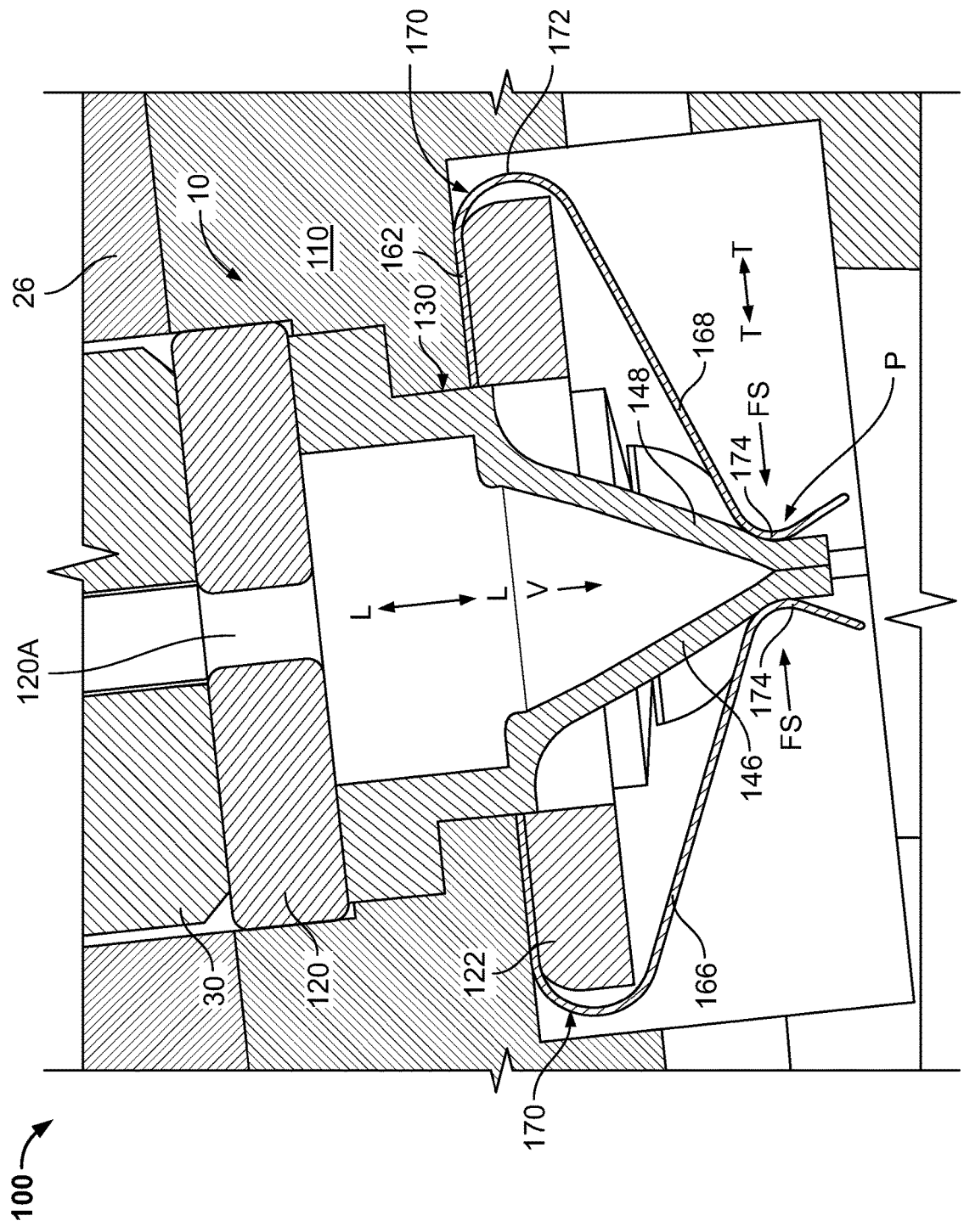
FIG. 3 is an enlarged, fragmentary, cross-sectional view of the needle trap charging module of FIG. 1 taken along the line 3-3 of FIG. 2 and showing the duckbill valve assembly in a closed position.
Figure 4:
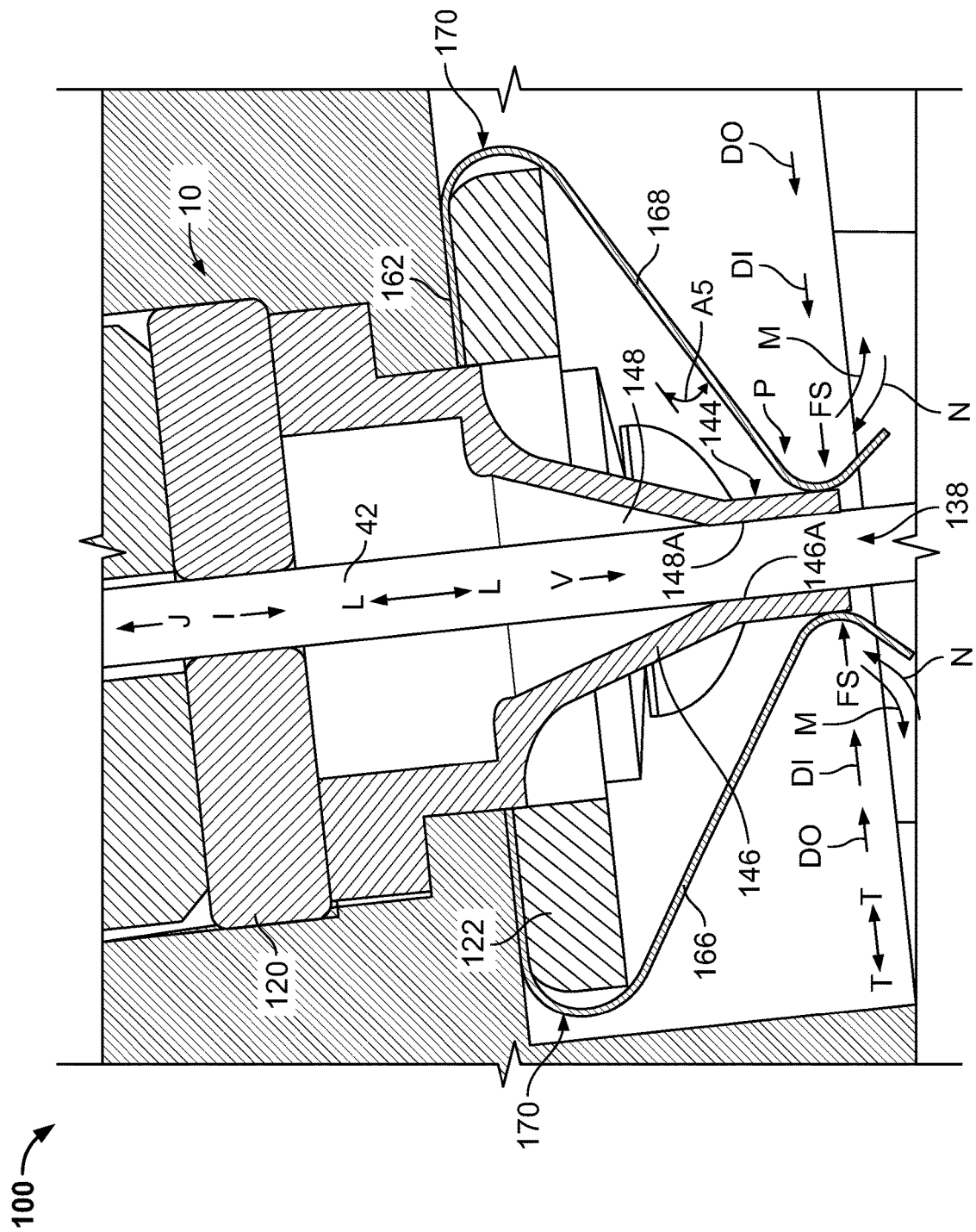
FIG. 4 is an enlarged, fragmentary, cross-sectional view of the needle trap charging module of FIG. 1 taken along the line 3-3 of FIG. 2 and showing the duckbill valve assembly in an open position with a needle inserted through the duckbill valve assembly.
Figure 5:
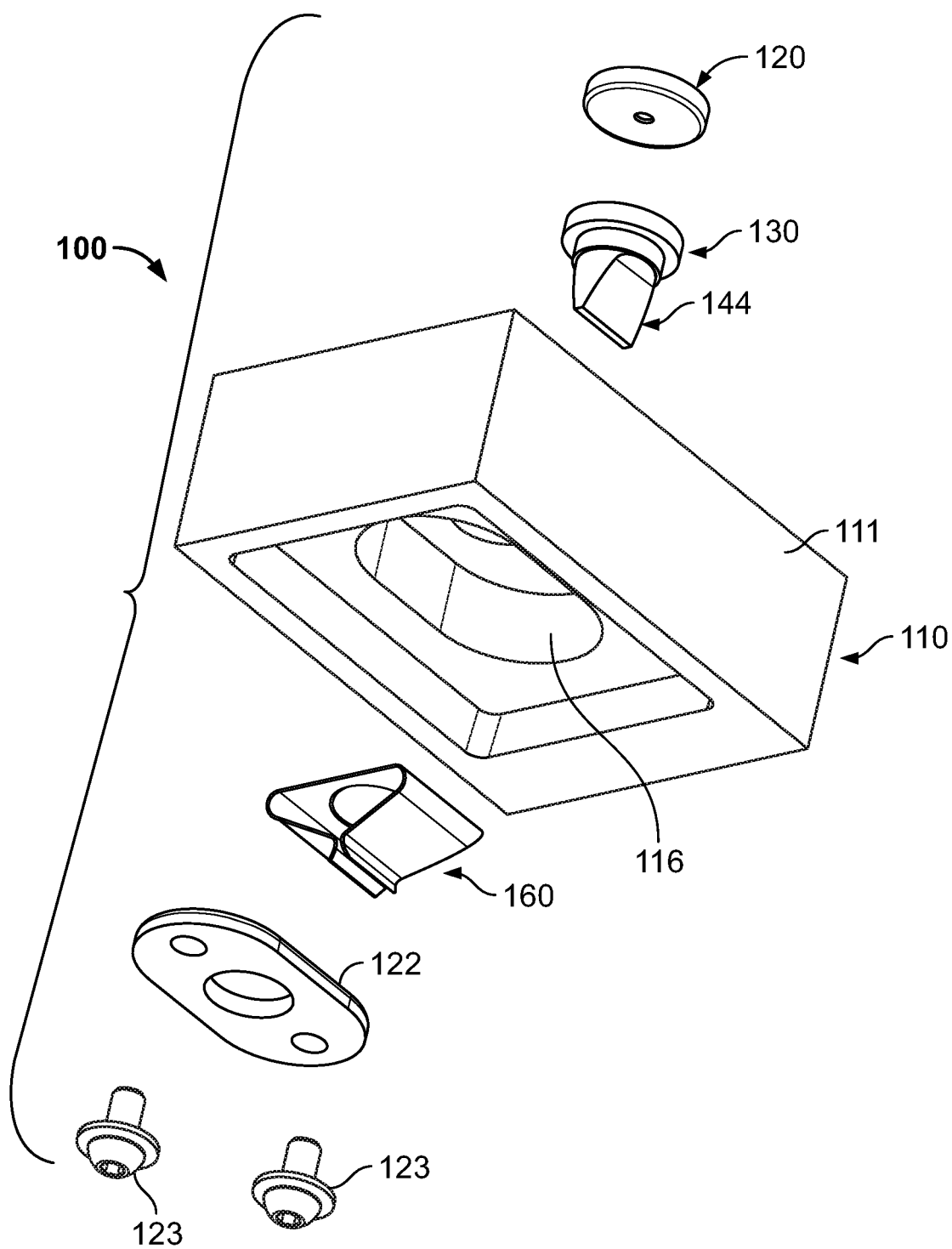
FIG. 5 is an exploded, bottom perspective view of the duckbill valve assembly of FIG. 1.
Figure 6:
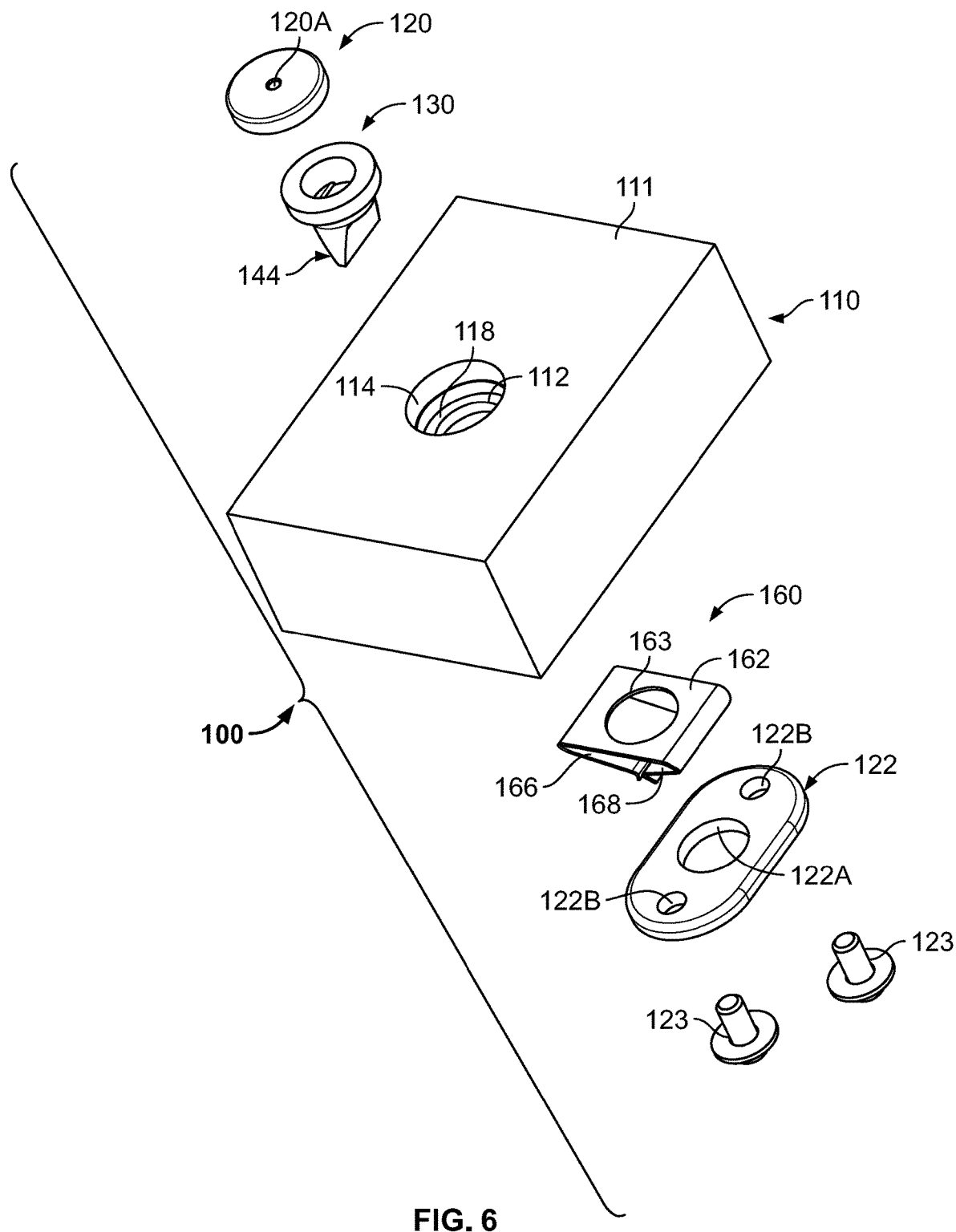
FIG. 6 is an exploded, top perspective view of the duckbill valve assembly of FIG. 1.
Figure 7:
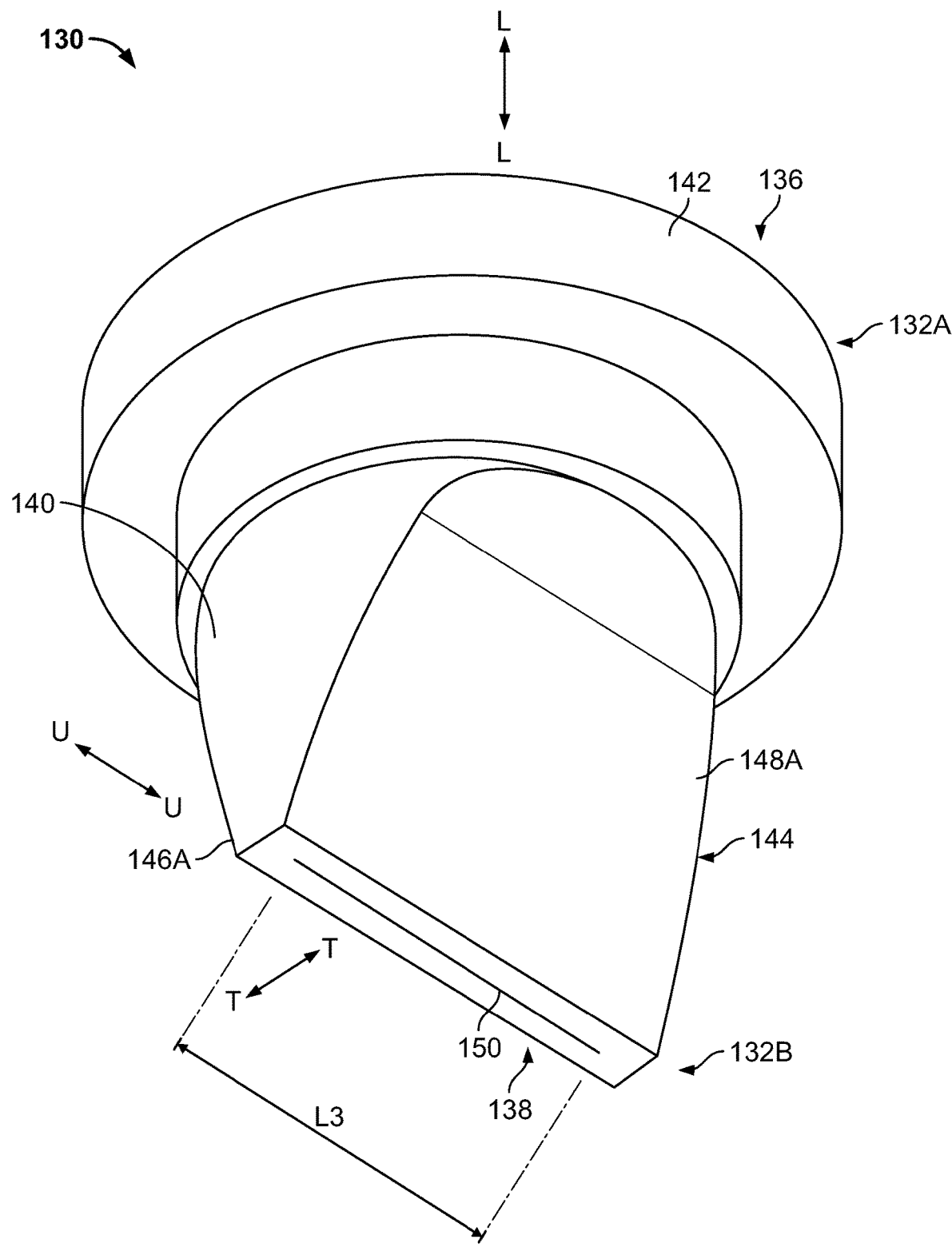
FIG. 7 is a bottom perspective view of a valve member forming a part of the duckbill valve assembly of FIG. 1.
Figure 8:
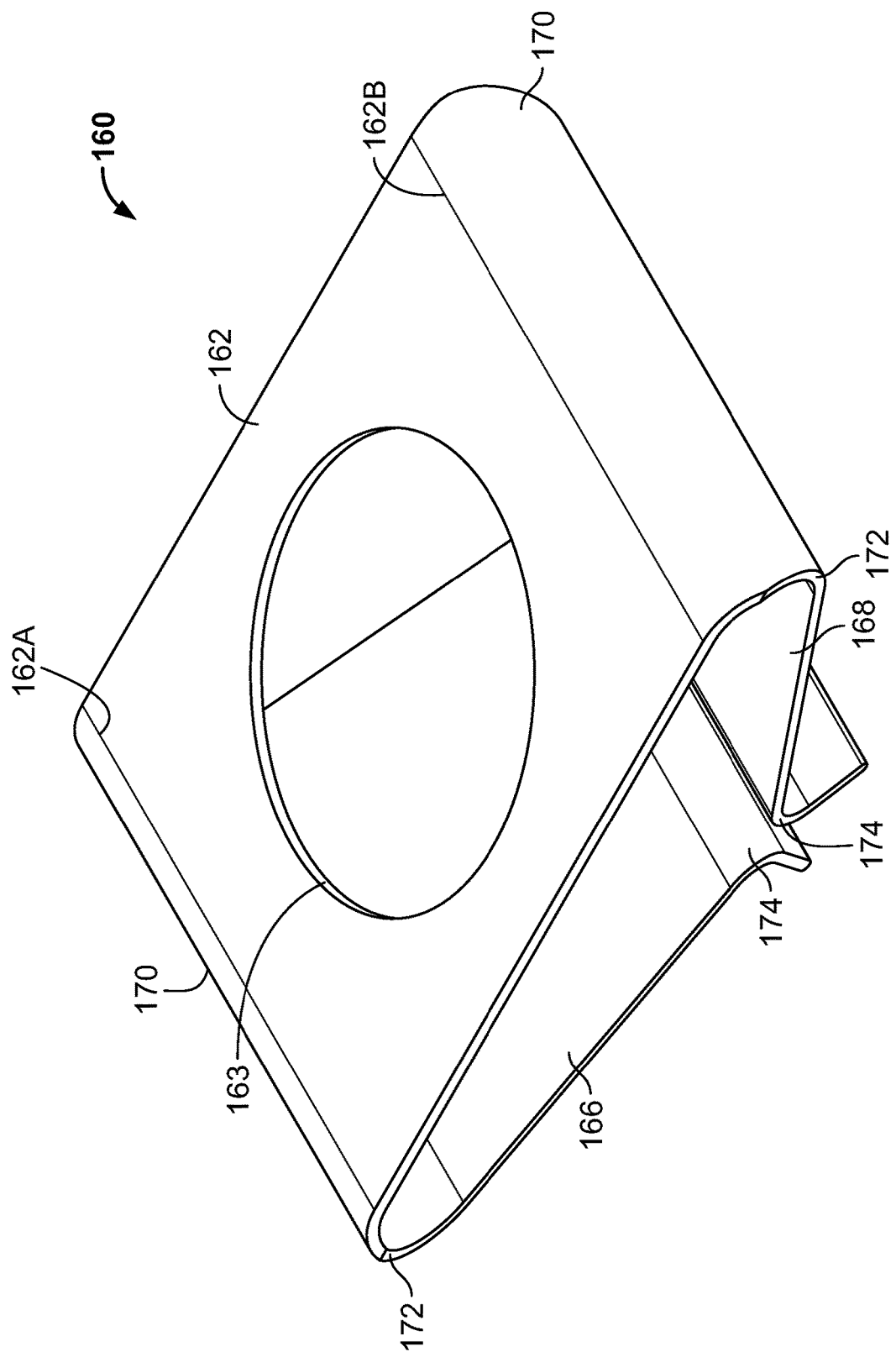
FIG. 8 is a top perspective view of a spring member forming a part of the duckbill valve assembly of FIG. 1.
Figure 9:
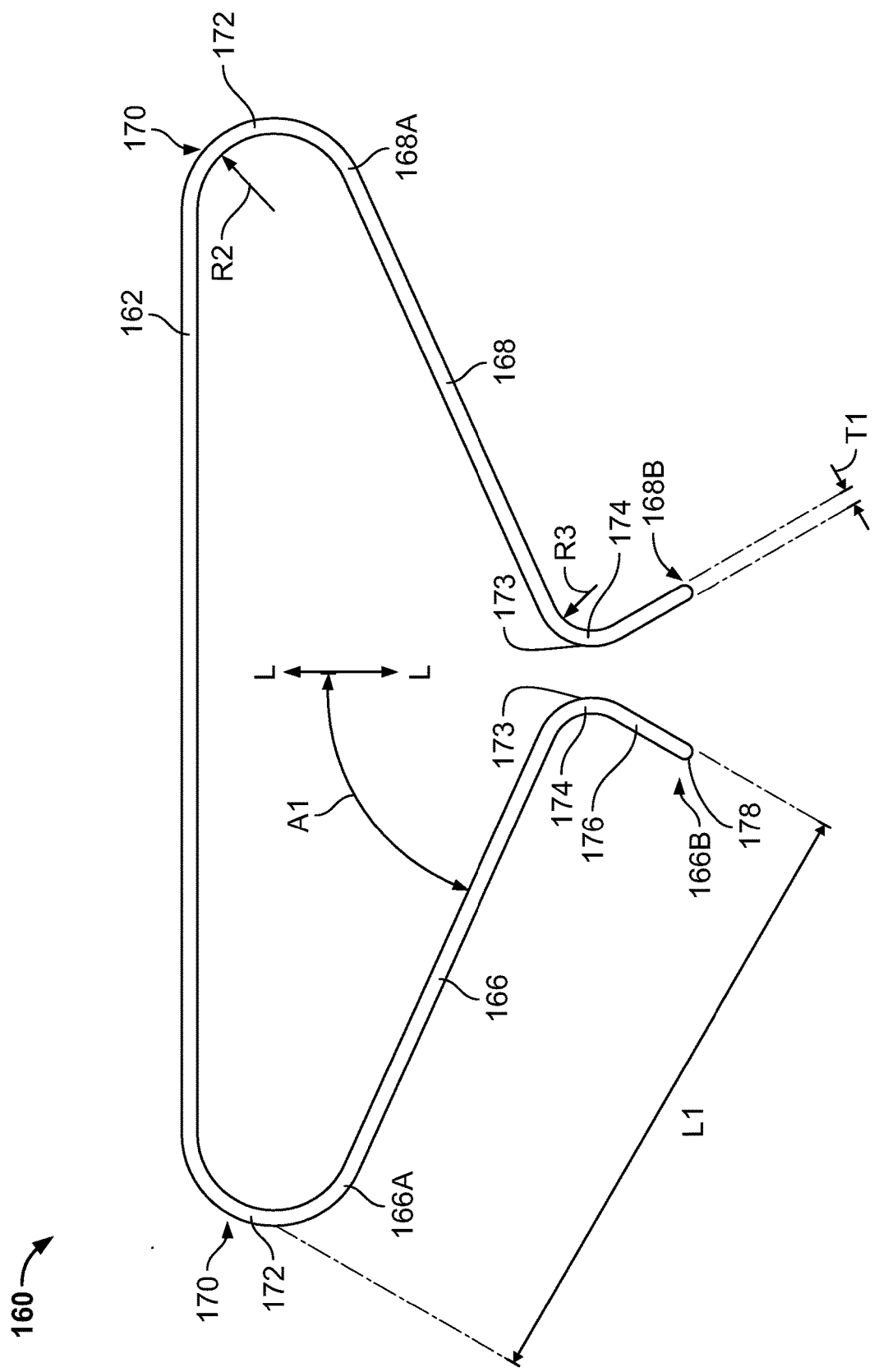
FIG. 9 is a front end view of the spring member of FIG. 8.

As shown in FIG. 3, the bends 172 curve around the side edges of the clamp plate 122.

The ring seal 120 is seated in the outer bore 114 in abutment with the proximal end 132A of the valve member 130.

The support 110 is clamped between the body 14 and the head 26 by the bolts 27. The needle guide 30 and the ring seal 38 are stacked over the ring seal 120. The end cap 36 is affixed (e.g., by fasteners) to the head 26. In this way, the valve member flange 142 and the ring seal 120 are clamped between the needle guide 30 and the support flange 118.

With the module 10 and the valve assembly 100 assembled as described above and shown in FIGS. 1-3, a distal portion of the duckbill 144 proximate the distal end 132B and the slit 150 is interposed between the opposed engagement portions 174 of the spring legs 166, 168 in a pinch region P. The contact surfaces 173 engage the outer surfaces 146A, 148A of the duckbill sidewalls 146, 148.

According to some embodiments, the spring legs 166, 168 are elastically radially outwardly displaced by the duckbill 144 so that the spring legs 166, 168 each exert a persistent, radially inwardly directed, compressive spring force FS on the distal end of the duckbill 144. The spring forces FS tend to press the closure surfaces 146B, 148B together and into sealing contact so that the slit 150 and the port 138 are positively held closed.

In use, the needle 42 (or other extraction or sampling device) is inserted into the module 10 as shown in FIG. 4. The needle 42 extends through the end cap 36, the ring seal 38, the needle guide passage 32, the ring seal 120, and the valve assembly 110 and into the head space 16. In this position, the ring seals 38, 120 form airtight seals around the needle 42 to prevent or inhibit the escape of gas from the headspace around the needle 42. In some embodiments, the inner diameters D2 (FIG. 2) of the ring seals 38, 120 are less than the outer diameter of the needle 42 so that the ring seals 38, 120 are elastically radially deformed and exert a persistent compressive, sealing load on the needle 42.

A gas sample can then be extracted from the head space 16 using the needle trap 40. The gas sample may be extracted using an suitable technique. For example, in some embodiments, the head space 16 is filled with a mixture of a carrier gas (e.g., helium) and a gas (including an analyte) from the vial 24 that enters the head space through the port 22. The gas mixture may be drawn into the needle 42 by a negative pressure that draws the mixture into the needle 42 through an distal end opening 42A, and out of the needle 42 through a proximal opening 42B. The gas exiting through the proximal needle opening may be flowed out through the exit port 34 in the module 10. The trap media 44 in the needle 42 is positioned such that the gas mixture flows through the media 44. The analyte is captured by (e.g., absorbed onto) the media. The needle trap 40 is thereby loaded or charged with the analyte.

In some embodiments, the vial 24 is a standard containing vial containing the analyte in a prescribed or known concentration. The charged needle trap 40 can then be used to inject the captured analyte into a gas chromatograph to test or calibrate the gas chromatograph.

The needle 42 can then be withdrawn from the module 10. Upon removal of the needle, the ring seals 38, 120 may remain open so that they no longer provide an airtight seal for the head space 16. However, the duckbill 144 will reclose its distal port 138, as discussed below, to provide an airtight seal for the head space 16.

With reference to FIG. 4, as the needle 42 is inserted into the valve assembly 100 in a needle insertion direction I, the distal tip of the needle 42 forces the sidewalls 146, 148 apart along the lateral axis T-T. The spring legs 166, 168 are thereby likewise forced apart along the lateral axis T-T. As the needle 42 penetrates the duckbill 144 at the pinch region P, the cantilevered spring legs 166, 168 pivot about their respective hinges 170 so that each spring leg 166, 168 and its engagement portion 174 are displaced or swing along an arcuate swing path M. Each swing path M extends in both the valve direction V and in a laterally outward direction DO. The laterally outward directions DO of the legs 166 and 168 extend in opposite directions. Each of the elastically displaced spring legs 166, 168 will continue to exert a spring force FS on the duckbill sidewalls 146, 148 tending to force them closed.

Once the needle 42 is fully inserted, each leg 166, 168 is deflected an angle A5 (FIG. 4) from its position in the closed position (FIG. 3) of the valve assembly 100 and its position in the open position (FIG. 4) of the valve assembly 100. In some embodiments, each angle A5 is in the range of from about 3 degrees to 5 degrees.

When the needle 42 is withdrawn from the valve assembly 100 in a needle withdrawal direction J, the sidewalls 146, 148 are permitted to come back together along the lateral axis T-T. The spring legs 166, 168 are thereby likewise permitted (and urged by the elastic spring forces FS) to move back towards one another along the lateral axis T-T. The valve distal port 138 is thereby resealed and closed by the elastic return force of the valve member 130, the force of a positive pressure differential (if any), and the return force of the spring legs 166, 168. The cantilevered spring legs 166, 168 pivot about their respective hinges 170 so that each spring leg 166, 168 and its engagement portions 174 are displaced or swing in both a direction opposite the valve direction V and in a laterally inward direction DI.

Once the valve assembly 100 has returned to its closed position, each of the elastically displaced spring legs 166, 168 will continue to exert a spring force FS on the duckbill sidewalls 146, 148 tending to force them closed. The spring legs 166, 168 thereby press the closure surfaces 146B, 148B together and into sealing contact so that the slit 150 and the port 138 are again positively held closed.

The spring member 160 serves to assist the duckbill 144 in sealing the distal port 138 and the slit 150. The assistance of the spring member 160 may be particularly beneficial in the even the pressure differential between the sealed volume or space (i.e., the chamber 16) and the opposing volume (i.e., on the proximal side of the valve member 130) is insufficient to reliable close the port 138 to prevent leakage of gas from the sealed volume through the duckbill 144. The spring member 160 thus enhances the duckbill seal but does not unduly impede the operation of the duckbill 144 or insertion and removal of the needle 42.

The valve assembly 100 can provide a number of advantages. The valve assembly can provide a more reliable gas tight seal when a needle 42 or the like is not inserted. The valve assembly 100 can thereby prevent or inhibit unintended leakage or gas discharge from the chamber 16.

The spring member 160 can permit the duckbill valve member 130 to effectively accommodate a larger range of needle sizes.

The valve assembly 100 can provide a more robust valve mechanism. The valve assembly 100 can permit the insertion of a needle or needles many times while maintaining adequate sealing performance. In some embodiments, the valve assembly 100 can accept more than one hundred needle insertions without requiring replacement of the valve assembly 100, the spring member 160 or the valve member 130.

The valve assembly 100 can use a duckbill valve member 130 that is available off-the-shelf and of known or conventional design. The inventive spring member 160 can be used without requiring modification to the duckbill valve member 130.

As the duckbill 144 transitions between its open and closed positions, the spring leg engagement portions 174 will slide along the duckbill sidewalls 146, 148. The rounded bearing surfaces 173 reduce wear on the sidewalls 146, 148.

The rounded surfaces 173 also allow the tip of the needle 42 to enter and exit the valve assembly 100 without exerting or introducing sharp stress concentrations on the sidewalls 146, 148 (e.g., rubber sidewalls) as would occur if sharp corners or edges were provided instead.

The rounded surfaces 173 also make it easier to slide a duckbill valve member 130 into the spring member 160. In some cases, it may be desirable to replace the valve member 130 with a new valve member 130. The valve member 130 may become worn out from use and the spring member 160 may have a longer service life than the valve member 130. The old valve member 130 can be removed from the proximal side of the valve assembly 10 and a new valve member 130 can be installed from the proximal side of the valve assembly 10, without removing the valve assembly 100 from the body 14, if desired.

The amount and dynamic profile of the spring forces FS applied to the duckbill 144 can be set or tuned by the selection of the material of the spring member 160, the dimensions of the spring member 160 (e.g., material thickness and width of the hinges 170, and the radius size and shape of the radiused hinges 170.

The radiused hinges 170 can provide a smoother, more uniform spring force profile as the spring legs 166, 168 deflect through their operational ranges of motion.

As discussed above, the cantilevered spring legs 166, 168 are deflected in arcs M that extend axially inward in the valve direction V (which is also the needle insertion direction I) and laterally outward in the direction DO. That is, the spring legs 166, 168 pivot down and out. This deflection profile provides a smooth transition from the closed position of the spring member 160 to its open position. The load transfer from the needle insertion in distributed over a longer stroke so that less pressure and friction is exerted on the sidewalls 146, 148 (e.g., rubber) as the spring member 160 is displaced from the closed position to the open position. As a result, damage to the duckbill 144 is reduced and the service life of the valve member 130 can be extended.

The relatively large and flat base portion 162 helps to prevent or inhibit rotation of spring member 160 relative to the duckbill 144. The relatively large and flat base portion 162 also helps to ensure that the valve member 130 and the spring member 160 are properly axially aligned or registered so that the engagement portions 174 pinch the duckbill 144 at the prescribed axial location.

Figure 10:
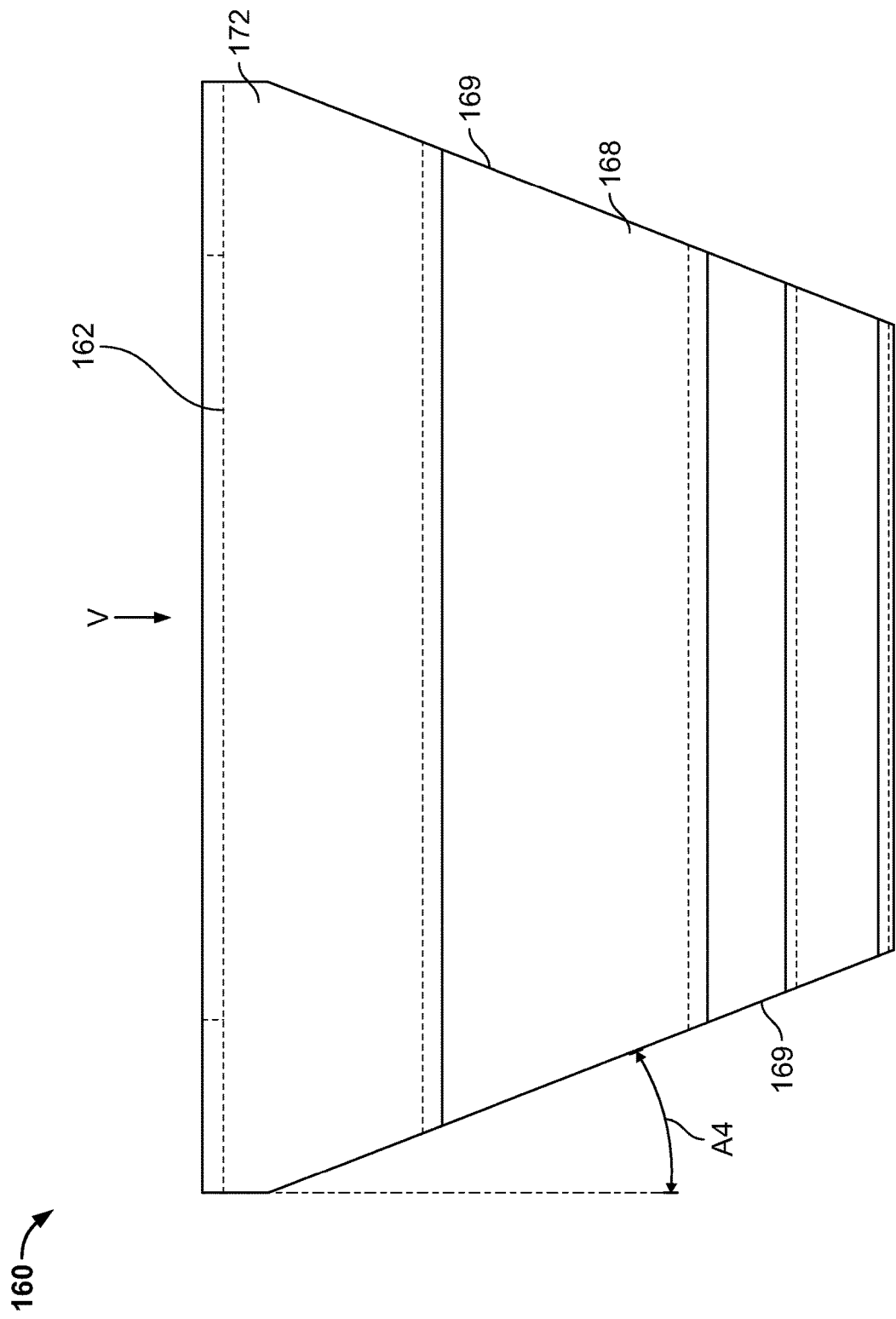
FIG. 10 is a side view of the spring member of FIG. 8.

In some embodiments and as shown in FIG. 10, each spring leg 166, 168 has opposed axially extending side edges 169 that taper toward one another in the valve direction V. This tapering of the spring legs 166, 168 allows the hinges 170 to be formed with a relatively large width that is greater than the width of the duckbill 144 without being wider than necessary to provide full contact between the spring legs and the sidewalls 146, 148 at the pinch region P. The spring member 160 can therefore be made with less material and a smaller form factor. In some embodiments, each edge 169 is tapered at an angle A4 in the range of from about 20 degrees to 22 degrees.

Figure 11:
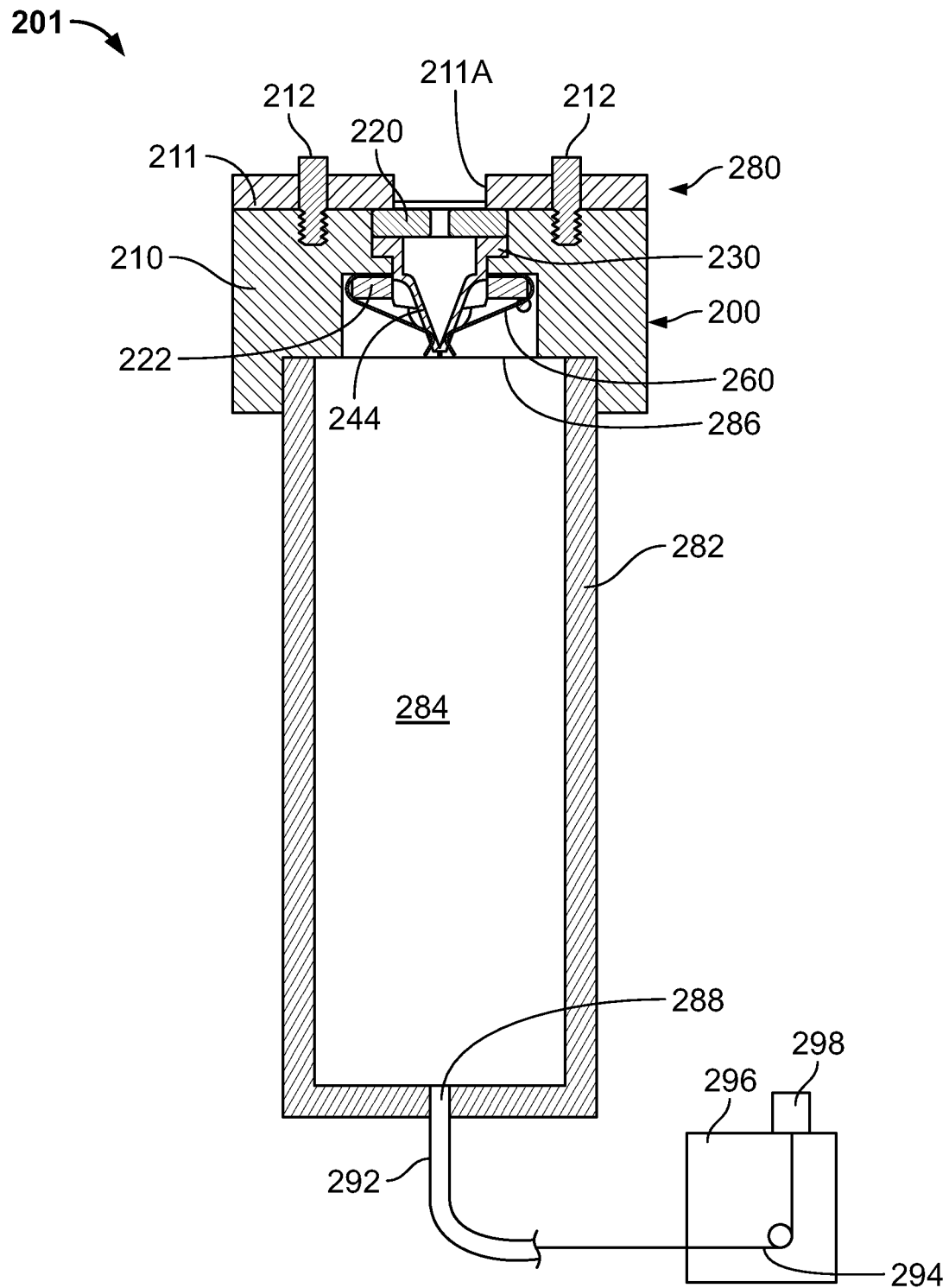
FIG. 11 is a cross-sectional view of a gas chromatographic system including a duckbill valve assembly according to embodiments of the technology.

With reference to FIG. 11, an apparatus 201 according to further embodiments of the technology is shown therein. The apparatus 201 is a gas chromatographic (GC) system. The GC system 201 includes a GC injection port 280. The GC injection port 280 incorporates a duckbill valve assembly 200 corresponding to the duckbill valve assembly 100. The duckbill valve assembly 200 operates as a gas tight, resealable septum to limit or prevent unintended discharge of a gas or gases from the GC injection port 280 in the same manner as described above for the module 10.

The GC injection port 280 includes a body 282 including a headspace or chamber 284. An inlet port 286 and an outlet port 288 fluidly communicate with the chamber 284.

The valve assembly 200 includes a support 210, an annular ring seal 220, a clamp plate 222, a duckbill valve member 230, and a spring member 260, which are constructed and assembled in the same manner as the support 110, the annular ring seal 120, the clamp plate 122, the duckbill valve member 130, and the spring member 160. The support 210 is affixed to the body 282 over the inlet port 286. An end cap 211 is secured to the support 210 over the ring seal 220 to secure and clamp the ring seal 220 and valve member 230 in place in the support 210. The end cap 211 includes an opening 211A. The end cap 211 may be removably and replaceably secured to the support 210 by bolts 212 or cooperating screw threads, for example.

The GC system 201 further includes a sample feed line 292, a column 294, a heater or oven 296 and a detector 298.

In use, a sample is injected into the chamber 284. The sample may be a gaseous sample including an analyte. The sample is injected using a needle or similar device that is inserted through the end cap opening 211A, the ring seal 220, and the duckbill 244. The needle may be a needle of a needle trap such as the needle trap 40 or a different type of device. It will be appreciated that when a needle (or other inserted device) is not inserted in the valve assembly 200, the duckbill 244 and the spring member 260 will cooperate as described above for the module 10 to maintain the duckbill 244 closed and sealed to prevent or inhibit leakage from the chamber 284 through the valve assembly 200. Likewise, when a needle (or other inserted device) is inserted in the valve assembly 200, the duckbill 244 and the spring member 260 will permit the insertion of the device while the ring seal 220 seals against the device to prevent or inhibit leakage from the chamber 284 through the valve assembly 200.

Once the sample has been injected into the chamber 284 using the needle, a carrier gas (the mobile phase; e.g., helium or nitrogen) sweeps the sample from the injection port chamber 284 through the feed line 292 to an inlet of the column 294, and through the column 294 to the detector 298, and thereafter to waste collection, a further detector or other desired destination. The oven 296 selectively heats the column 294 before, during and/or after the sample is passed therethrough in order to control the temperature of the column 294 and the sample. The column 294 includes an inner layer or packing of a selected stationary phase in or on the inner wall of the column 294. The gaseous compounds of the sample interact with the stationary phase; having a different affinity for each component, retains the different components of the sample for different times. As a result, the different compounds elute at different times and take different amounts of time to pass through and exit the column 294 to the detector 298 (i.e., the components have different retention times within the column 294). The detector 298 monitors the outlet stream from the column 294 to detect or sense the time at which each analyte component emerges from the column 294 and reaches the detector 298, and/or the amount of the analyte. The detection data from the detector 298 may be stored and processed by a chromatographic data processing system. Various parameters of the process may be controlled by a controller, including the carrier gas flow rate (using a flow controller), the column and/or mobile phase temperatures (using the GC oven 296), and the sample injection timing and rate.

Figure 12:
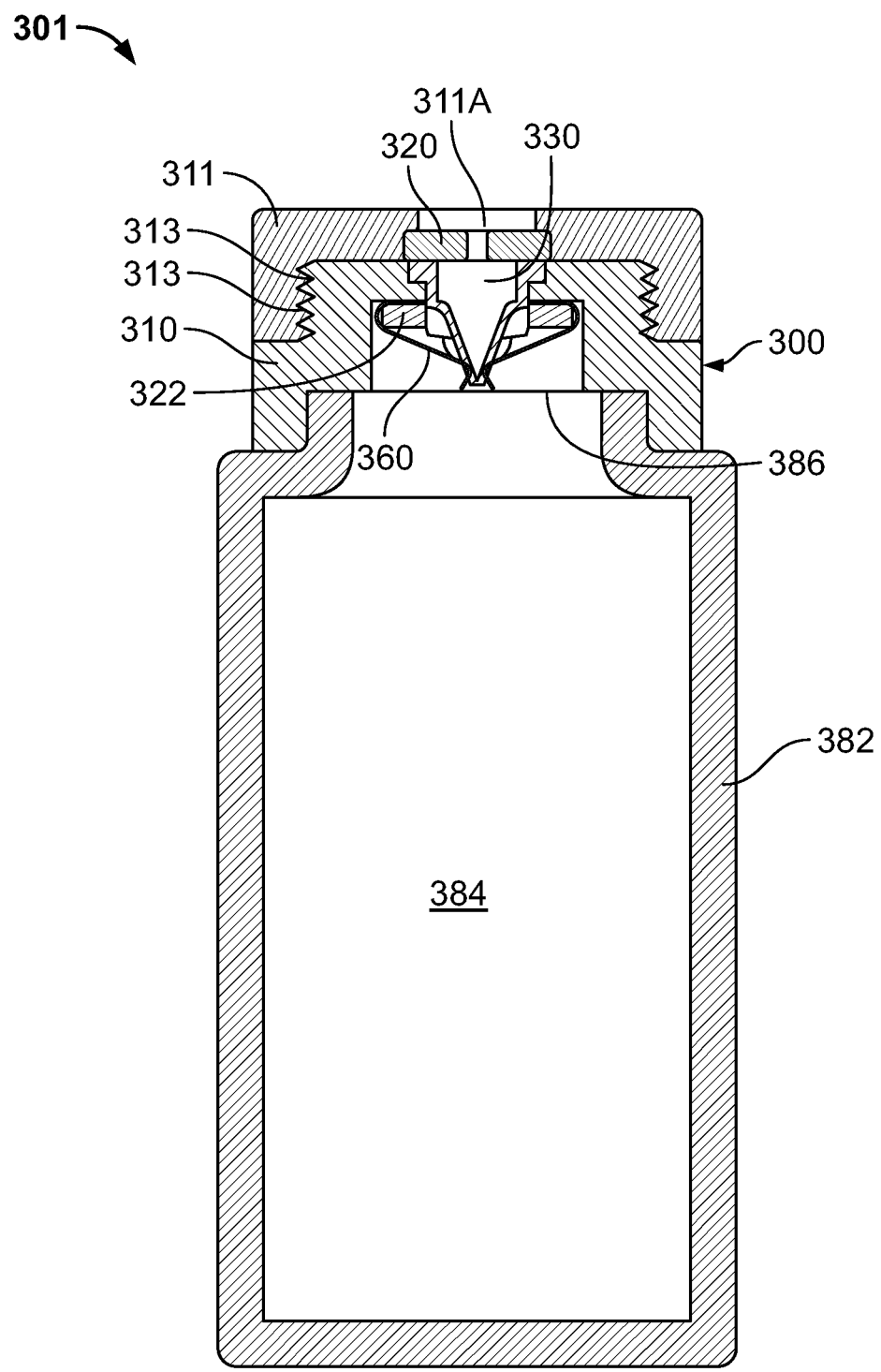
FIG. 12 is a cross-sectional view of a vial including a duckbill valve assembly according to embodiments of the technology.

With reference to FIG. 12, an apparatus 301 according to further embodiments of the technology is shown therein. The apparatus 301 is a sample vial or container. The vial 301 incorporates a duckbill valve assembly 300 corresponding to the duckbill valve assembly 100.

The vial 301 includes a body 382 including a chamber 384. An inlet port 386 fluidly communicates with the chamber 384.

The valve assembly 300 includes a support 310, an annular ring seal 320, a clamp plate 322, a duckbill valve member 330, and a spring member 360, which are constructed and assembled in the same manner as the support 110, the annular ring seal 120, the clamp plate 122, the duckbill valve member 130, and the spring member 160. The support 310 is affixed to the body 382 over the inlet port 386. An end cap 311 is secured to the support 310 over the ring seal 320 to secure and clamp the ring seal 320 and valve member 330 in place in the support 310. The end cap 211 includes an opening 311A. The end cap 311 may be removably and replaceably secured to the support 310 by bolts or cooperating screw threads 313, for example.

The duckbill valve assembly 300 operates as a gas tight, resealable septum to limit or prevent unintended discharge of a gas or gases from the vial 301 in the same manner as described above for the module 10.

Duckbill valve assemblies as disclosed herein and in accordance with embodiments of the technology may also be used in apparatus and applications wherein the valve assembly opens and closes to receive elongate members other than needles.

Duckbill valve assemblies as disclosed herein and in accordance with embodiments of the technology may also be used in apparatus and applications wherein the valve assembly opens and closes to permit flow of a fluid through the valve assembly in response to a prescribed pressure differential between the pressure on the proximal side of the duckbill 144 and the distal side of the duckbill 144. For example, the valve assembly 100 may open in response to a pressure differential exceeding a prescribed pressure differential and permit flow of a fluid therethrough, even in the absence of any force from a needle or other mechanical device tending to force the duckbill 144 open. The valve assembly can operate as a self-sealing, non-return axial flow valve.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A duckbill valve assembly for use with an elongate member, the duckbill valve assembly comprising:
a duckbill valve having a longitudinal axis, a lateral axis transverse to the longitudinal axis, and opposed proximal and distal ends spaced apart along the longitudinal axis, the duckbill valve defining a valve direction extending from the proximal end to the distal end, the duckbill valve including:
a first port at the proximal end; and
first and second opposed sidewalls, wherein the first and second sidewalls taper inwardly toward one another in the valve direction to form a duckbill structure, the duckbill structure including a slit proximate the distal end;
wherein the duckbill valve is transitionable from a closed position, wherein the slit is closed, and an open position, wherein the first and second sidewalls are laterally separated proximate the slit to form a second port;
a spring member including a spring leg disposed laterally adjacent the first side wall, wherein the spring leg exerts a spring load on the first sidewall, the spring load forcing the first and second sidewalls together to maintain the slit in the closed position; and
an elastomeric, annular supplemental ring seal including a through opening, wherein the supplemental ring seal has an inner diameter that is less than an outer diameter of the elongate member;
wherein the duckbill valve assembly is configured to receive the elongate member such that, when the elongate member is inserted through the duckbill valve assembly:
the first and second sidewalls are displaced laterally outward to open the slit, and the spring leg is displaced in the valve direction and in a laterally outward direction; and
the elongate member extends through the through opening of the supplemental ring seal and thereby elastically radially deforms the supplemental ring seal, and the supplemental ring seal exerts a persistent compressive sealing load on the elongate member to form an airtight seal around the elongate member.

2. The duckbill valve assembly of claim 1 wherein the spring member includes:
a base portion; and
a spring leg cantilevered from the base portion, the spring leg having a proximal end joined to the base portion and a distal end that applies the spring load to the first sidewall.

3. The duckbill valve assembly of claim 2 including a radiused bend forming a hinge connecting the proximal end of the spring leg to the base portion.

4. The duckbill valve assembly of claim 3 wherein the radiused bend has a radius in the range of from about 0.7 mm to 0.9 mm.

5. The duckbill valve assembly of claim 2 wherein:
the spring leg includes a rounded bearing surface proximate the distal end of the spring leg; and
the rounded bearing surface engages the first sidewall.

6. The duckbill valve assembly of claim 5 wherein the rounded bearing surface has a radius in the range of from about 0.4 mm to 0.6 mm.

7. The duckbill valve assembly of claim 2 wherein the spring leg has opposed axially extending side edges that taper inwardly in a direction from the base portion to the distal end.

8. The duckbill valve assembly of claim 2 including a support and a clamp member, wherein the base portion is clamped between the support and the clamp member.

9. The duckbill valve assembly of claim 1 wherein:
the spring member includes a second spring leg disposed laterally adjacent the second side wall and laterally opposite the first spring leg;
the second spring leg exerts a second spring load on the second sidewall, the first and second spring loads forcing the first and second sidewalls together to maintain the slit in the closed position;
wherein the duckbill valve assembly is configured such that, when the first and second sidewalls are displaced laterally outward to open the slit, the first and second spring legs are displaced in the valve direction and in opposing laterally outward directions.

10. The duckbill valve assembly of claim 9 wherein:
the spring member includes a base portion having opposed first and second side edges;
the first spring leg is cantilevered from the first side edge of the base portion, the first spring leg having a proximal end joined to the base portion and a distal end that applies the first spring load to the first sidewall; and
the second spring leg is cantilevered from the second side edge of the base portion, the second spring leg having proximal end joined to the base portion and a distal end that applies the second spring load to the second sidewall.

11. The duckbill valve assembly of claim 10 including:
a first radiused bend forming a hinge connecting the proximal end of the first spring leg to the first side edge of the base portion; and
a second radiused bend forming a hinge connecting the proximal end of the second spring leg to the second side edge of the base portion.

12. The duckbill valve assembly of claim 11 wherein the spring member is monolithic.

13. A gas chromatograph (GC) system comprising:
a GC injection port including:
a chamber; and
a duckbill valve assembly positioned to control fluid flow into and/or out of the chamber, wherein the duckbill valve assembly includes:
a duckbill valve having a longitudinal axis, a lateral axis transverse to the longitudinal axis, and opposed proximal and distal ends spaced apart along the longitudinal axis, the duckbill valve defining a valve direction extending from the proximal end to the distal end, the duckbill valve including:
a first port at the proximal end; and
first and second opposed sidewalls, wherein the first and second sidewalls taper inwardly toward one another in the valve direction to form a duckbill structure, the duckbill structure including a slit proximate the distal end;
wherein the duckbill valve is transitionable from a closed position, wherein the slit is closed, and an open position, wherein the first and second sidewalls are laterally separated proximate the slit to form a second port; and
a spring member including a spring leg disposed laterally adjacent the first side wall, wherein the spring leg exerts a spring load on the first sidewall, the spring load forcing the first and second sidewalls together to maintain the slit in the closed position;

wherein the duckbill valve assembly is configured such that, when the first and second sidewalls are displaced laterally outward to open the slit, the spring leg is displaced in the valve direction and in a laterally outward direction;

a column fluidly connected to the chamber; and a detector fluidly connected to the column;

wherein the GC system is configured to sweep a sample from the chamber, through the column and to the detector.

14. A method for handling a fluid, the method comprising:
providing an apparatus comprising:
a chamber; and
a duckbill valve assembly positioned to control fluid flow into and/or out of the chamber, wherein the duckbill valve assembly includes:
a duckbill valve having a longitudinal axis, a lateral axis transverse to the longitudinal axis, and opposed proximal and distal ends spaced apart along the longitudinal axis, the duckbill valve defining a valve direction extending from the proximal end to the distal end, the duckbill valve including:
a first port at the proximal end; and
first and second opposed sidewalls, wherein the first and second sidewalls taper inwardly toward one another in the valve direction to form a duckbill structure, the duckbill structure including a slit proximate the distal end;
wherein the duckbill valve is transitionable from a closed position, wherein the slit is closed, and an open position, wherein the first and second sidewalls are laterally separated proximate the slit to form a second port; and
a spring member including a spring leg disposed laterally adjacent the first side wall, wherein the spring leg exerts a spring load on the first sidewall, the spring load forcing the first and second sidewalls together to maintain the slit in the closed position;
wherein the duckbill valve assembly is configured such that, when the first and second sidewalls are displaced laterally outward to open the slit, the spring leg is displaced in the valve direction and in a laterally outward direction;
inserting a needle through the duckbill valve assembly and into the chamber;
using the needle, extracting a fluid from the chamber and/or introducing a fluid into the chamber through the needle; and thereafter
removing the needle from the duckbill valve assembly.

15. The method of claim 14 wherein:
the needle forms a part of a needle trap;
the needle trap further includes a trap media disposed in the needle; and
the method includes, while the needle is inserted through the duckbill valve assembly, flowing the fluid through the trap media in the needle such that an analyte in the fluid is captured in the trap media.

16. The method of claim 14 wherein:
the duckbill valve assembly further includes an elastomeric, annular supplemental ring seal including a through opening, wherein the supplemental ring seal has an inner diameter that is less than an outer diameter of the needle;
the step of inserting the needle through the duckbill valve assembly and into the chamber includes inserting the needle through the through opening of the supplemental ring seal and thereby elastically radially deforming the supplemental ring seal; and
during the step of extracting a fluid from the chamber and/or introducing a fluid into the chamber through the needle, the supplemental ring seal exerts a persistent compressive sealing load on the needle to form an airtight seal around the needle.

17. A duckbill valve assembly comprising:
a duckbill valve having a longitudinal axis, a lateral axis transverse to the longitudinal axis, and opposed proximal and distal ends spaced apart along the longitudinal axis, the duckbill valve defining a valve direction extending from the proximal end to the distal end, the duckbill valve including:
a first port at the proximal end; and
first and second opposed sidewalls, wherein the first and second sidewalls taper inwardly toward one another in the valve direction to form a duckbill structure, the duckbill structure including a slit proximate the distal end;
wherein the duckbill valve is transitionable from a closed position, wherein the slit is closed, and an open position, wherein the first and second sidewalls are laterally separated proximate the slit to form a second port; and
a spring member including:
a first spring leg disposed laterally adjacent the first side wall, wherein the first spring leg exerts a first spring load on the first sidewall; and
a second spring leg disposed laterally adjacent the second side wall and laterally opposite the first spring leg, wherein the second spring leg exerts a second spring load on the second sidewall;
wherein the first and second spring loads force the first and second sidewalls together to maintain the slit in the closed position;
wherein the duckbill valve assembly is configured such that, when the first and second sidewalls are displaced laterally outward to open the slit, the first and second spring legs are displaced in the valve direction and in opposing laterally outward directions; and
wherein:
the spring member includes a base portion having opposed first and second side edges;
the first spring leg is cantilevered from the first side edge of the base portion, the first spring leg having a proximal end joined to the base portion and a distal end that applies the first spring load to the first sidewall; and
the second spring leg is cantilevered from the second side edge of the base portion, the second spring leg having proximal end joined to the base portion and a distal end that applies the second spring load to the second sidewall; and
the spring member is unitarily formed.

18. The duckbill valve assembly of claim 17 wherein the spring member is monolithic.

19. A duckbill valve assembly comprising:
a duckbill valve having a longitudinal axis, a lateral axis transverse to the longitudinal axis, and opposed proximal and distal ends spaced apart along the longitudinal axis, the duckbill valve defining a valve direction extending from the proximal end to the distal end, the duckbill valve including:
a first port at the proximal end; and
first and second opposed sidewalls, wherein the first and second sidewalls taper inwardly toward one another in the valve direction to form a duckbill structure, the duckbill structure including a slit proximate the distal end;
wherein the duckbill valve is transitionable from a closed position, wherein the slit is closed, and an open position, wherein the first and second sidewalls are laterally separated proximate the slit to form a second port; and
a spring member including a spring leg disposed laterally adjacent the first side wall, wherein the spring leg exerts a spring load on the first sidewall, the spring load forcing the first and second sidewalls together to maintain the slit in the closed position;
wherein the duckbill valve assembly is configured such that, when the first and second sidewalls are displaced laterally outward to open the slit, the spring leg is displaced in the valve direction and in a laterally outward direction; and
wherein the spring member includes:
a base portion; and
a spring leg cantilevered from the base portion, the spring leg having a proximal end joined to the base portion and a distal end that applies the spring load to the first sidewall; and
wherein the spring leg has opposed axially extending side edges that taper inwardly in a direction from the base portion to the distal end.

* * * * *